(12) United States Patent
Mori

(10) Patent No.: US 11,439,589 B2
(45) Date of Patent: Sep. 13, 2022

(54) EMULSION EYEDROPS

(71) Applicant: SENJU PHARMACEUTICAL CO., LTD., Osaka (JP)

(72) Inventor: Yasuhiro Mori, Osaka (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/348,538

(22) PCT Filed: Nov. 16, 2017

(86) PCT No.: PCT/JP2017/041230
§ 371 (c)(1),
(2) Date: May 9, 2019

(87) PCT Pub. No.: WO2018/092835
PCT Pub. Date: May 24, 2018

(65) Prior Publication Data
US 2020/0054554 A1  Feb. 20, 2020

(30) Foreign Application Priority Data

Nov. 17, 2016 (JP) .............................. JP2016-224349

(51) Int. Cl.
| | |
|---|---|
| A61K 9/00 | (2006.01) |
| A61K 9/107 | (2006.01) |
| A61K 47/32 | (2006.01) |
| A61K 47/44 | (2017.01) |

(52) U.S. Cl.
CPC .......... *A61K 9/0048* (2013.01); *A61K 9/1075* (2013.01); *A61K 47/32* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 4,497,829 | A * | 2/1985 | Sloviter | A61K 9/0026 514/672 |
| 5,474,979 | A | 12/1995 | Ding et al. | |
| 6,114,319 | A | 9/2000 | Kimura et al. | |
| 2008/0139652 | A1* | 6/2008 | Sakai | A61P 27/06 514/559 |
| 2008/0146678 | A1* | 6/2008 | Nishioku | A61Q 19/00 514/772.4 |
| 2010/0137252 | A1 | 6/2010 | Matsumura et al. | |
| 2012/0135947 | A1 | 5/2012 | Shikamura | |
| 2014/0328914 | A1* | 11/2014 | Sheskey | F01M 1/16 424/480 |
| 2016/0101050 | A1* | 4/2016 | Lee | A61K 9/1075 424/400 |

FOREIGN PATENT DOCUMENTS

| | | |
|---|---|---|
| JP | 10-500414 | 1/1998 |
| JP | 11-29483 | 2/1999 |
| JP | 2016-519162 | 6/2016 |
| WO | 95/31211 | 11/1995 |
| WO | 2005/044276 | 5/2005 |
| WO | 2006/075743 | 7/2006 |
| WO | 2009/063692 | 5/2009 |
| WO | 2010/064636 | 6/2010 |
| WO | 2016/127022 | 8/2016 |

OTHER PUBLICATIONS

Jumaa et al (Physicochemical properties of chitosan-lipid emulsions and their stability during the autoclaving process. International Journal of Pharmaceutics 183 (1999) 175-184), (Year: 1999).*
Tamilvanan et al (Stability Assessment of Injectable Castor Oil-Based Nano-sized Emulsion Containing Cationic Droplets Stabilized by Poloxamer-Chitosan Emulsifier Films. AAPS PharmSciTech, vol. 11, No. 2, Jun. 2010) (Year: 2010).*
International Search Report dated Jan. 23, 2018 in International Application No. PCT/JP2017/041230.

* cited by examiner

*Primary Examiner* — Jake M Vu
(74) *Attorney, Agent, or Firm* — Wenderoth, Lind & Ponack, L.L.P.

(57) ABSTRACT

Provided are: emulsion eyedrops which have no concern with possible corneal injury induced by a nonionic surfactant, have excellent thermal stability and physical stability and can contain a sparingly water-soluble drug in an increased amount; and an emulsion eyedrops stabilization method. The emulsion eyedrops contain castor oil and poly(vinyl alcohol), wherein the concentration of castor oil is 5 to 20 w/v %, the concentration of poly(vinyl alcohol) is 2 to 7 w/v %, and the ratio of the weight of castor oil to the weight of poly(vinyl alcohol) is 1.2 to 5. The emulsion eyedrops stabilization method is characterized by preparing emulsion eyedrops containing castor oil and poly(vinyl alcohol), wherein the concentration of castor oil is 5 to 20 w/v %, the concentration of poly(vinyl alcohol) is 2 to 7 w/v %, and the ratio of the weight of castor oil to the weight of poly(vinyl alcohol) is 1.2 to 5.

6 Claims, No Drawings

EMULSION EYEDROPS

TECHNICAL FIELD

The present invention generally relates to emulsion eyedrops, more specifically relates to oil-in-water-type emulsion eyedrops.

BACKGROUND ART

Heretofore, emulsion eyedrops are known as eyedrops containing a sparingly water-soluble drug. As an emulsifying agent for emulsion eyedrops, a nonionic surfactant has been generally used. For example, JP 11-029483 A (Patent Literature 1) discloses an emulsified composition which contains difluprednate as a sparingly water-soluble drug, castor oil as an oil, water, and polysorbate (which is a nonionic surfactant) as an emulsifying agent.

WO 2009/063692 A1 (Patent Literature 2) discloses a drug-containing fat emulsion containing, as constituent components, at least a sparingly water-soluble drug, an oil or fat, an emulsifying agent and water, the drug-containing fat emulsion being characterized in that the content of the oil or fat is 0.05 to 2 mg/mL, the ratio of the weight of the drug to the weight of the oil or fat (i.e., drug/oil or fat) is 0.01 to 20 (wherein the total content of the drug and the oil or fat is up to 5 mg/mL), and the ratio of the weight of the emulsifying agent to the weight of the oil or fat (i.e., emulsifying agent/oil or fat) is 1 to 300.

WO 2005/044276 A1 (Patent Literature 3) discloses eyedrops composed of an oil-in-water type emulsion containing a prostaglandin $F_{2\alpha}$ derivative, an oil, a water-soluble polymer and water.

CITATION LIST

Patent Literature

Patent Literature 1: Japanese Patent Application Laid-Open Publication No. H11-029483 A
Patent Literature 2: WO 2009/063692 A1
Patent Literature 3: WO 2005/044276 A1

SUMMARY OF THE INVENTION

Technical Problem

A nonionic surfactant is highly irritative to an ocular mucous membrane. Therefore, when a composition containing a nonionic surfactant as an emulsifying agent at a high concentration is used as eyedrops, corneal disorders may be induced by the nonionic surfactant.

If the content of an oily component is smaller than the content of an emulsifying agent as in the case of the drug-containing fat emulsion disclosed in Patent Literature 2, the problem that the content of a sparingly water-soluble drug cannot be increased may arise.

Patent Literature 3 discloses emulsion eyedrops containing a medium-chain fatty acid triglyceride and a water-soluble polymer that serves as an emulsifying agent. However, when the content of the oily component is larger than that of the emulsifying agent, a nonionic surfactant is contained as the emulsifying agent and therefore corneal disorders may be induced by the nonionic surfactant. When no nonionic surfactant is contained, on the other hand, the content of the oily component is adjusted to a lower level than that of the emulsifying agent. In this case, it is also impossible to increase the content of a sparingly water-soluble drug, as in the case of Patent Literature 2. Furthermore, although the solubility of a drug upon warming is considered, the solubility of the emulsion itself is not considered.

Eyedrops are generally sterilized by filtration, regardless of the type of the eyedrops, i.e., whether the eyedrops are water-based eyedrops or emulsion eyedrops. Eyedrops which cannot be sterilized by filtration are sterilized by heating. However, an emulsion composition is generally unstable against heat. Therefore, emulsion eyedrops that are sterilized by heating is required to acquire particularly superior thermal stability such that particle diameter cannot be changed upon heating. Furthermore, emulsion eyedrops should be formulated such that particle diameter can be hardly changed during the storage for a long period, and therefore are required to have excellent thermal stability and physical stability.

The object of the present invention is to provide emulsion eyedrops which have a small risk of developing corneal disorders, have excellent thermal stability and physical stability and can contain a sparingly water-soluble drug in an increased amount.

Solution to Problem

The present inventors have made extensive and intensive studies in order to solve the above-mentioned problems. As a result, it is found for the first time that all of the problems can be solved by emulsion eyedrops which contain castor oil and poly(vinyl alcohol), wherein the concentration of castor oil is 5 to 20 w/v %, the concentration of poly(vinyl alcohol) is 2 to 7 w/v %, and the ratio of the weight of castor oil to the weight of poly(vinyl alcohol) (also referred to as a "C/P" ratio, hereinafter) is 1.2 to 5.

On the basis of the above-mentioned findings, the emulsion eyedrops according to the present invention are constituted as follows.

[1] Emulsion eyedrops comprising castor oil and poly (vinyl alcohol), wherein
the concentration of the castor oil is 5 to 20 w/v %,
the concentration of the poly(vinyl alcohol) is 2 to 7 w/v %, and
the ratio of the weight of the castor oil to the weight of the poly(vinyl alcohol) is 1.2 to 5.

[2] The emulsion eyedrops according to [1], wherein substantially no nonionic surfactant is contained.

[3] The emulsion eyedrops according to any one of [1] and [2], wherein a sparingly water-soluble drug is further contained.

[4] The emulsion eyedrops according to any one of [1] to [3], wherein, when the emulsion eyedrops are sterilized in an autoclave at 121° C. for 20 minutes, the rate of change in the average particle diameter of oil droplets contained in the emulsion eyedrops before and after the sterilization in the autoclave is less than 3%.

[5] The emulsion eyedrops according to [4], wherein the average particle diameter of oil droplets contained in the emulsion eyedrops before the sterilization in the autoclave is 100 to 200 nm.

[6] The emulsion eyedrops according to any one of [1] to [5], wherein, when the emulsion eyedrops are centrifuged at 20000×g for 20 minutes, the emulsion eyedrops are homogeneous.

[7] An emulsion eyedrops stabilization method, comprising the step of preparing emulsion eyedrops containing castor oil and poly(vinyl alcohol), wherein:

the concentration of the castor oil is 5 to 20 w/v %;

the concentration of the poly(vinyl alcohol) is 2 to 7 w/v %; and the ratio of the weight of the castor oil to the weight of the poly(vinyl alcohol) is 1.2 to 5.

[8] The stabilization method according to [7], wherein the emulsion eyedrops contain substantially no nonionic surfactant.

[9] The stabilization method according to [7] or [8], wherein the emulsion eyedrops further contain a sparingly water-soluble drug.

[10] The stabilization method according to any one of [7] to [9], wherein, when the emulsion eyedrops are sterilized in an autoclave at 121° C. for 20 minutes, the rate of change in the average particle diameter of oil droplets contained in the emulsion eyedrops before and after the sterilization in the autoclave is less than 3%.

[11] The stabilization method according to [10], wherein the average particle diameter of oil droplets contained in the emulsion eyedrops before the sterilization in the autoclave is 100 to 200 nm.

[12] The stabilization method according to any one of [7] to [11], wherein, when the emulsion eyedrops are centrifuged at 20000×g for 20 minutes, the emulsion eyedrops are homogeneous.

Advantageous Effects of the Invention

As mentioned above, according to the present invention, the emulsion eyedrops according to the present invention contain no nonionic surfactant, and therefore it becomes possible to provide emulsion eyedrops having a reduced risk of developing corneal disorders. Furthermore, the emulsion eyedrops according to the present invention have an extremely small change in particle diameter when the emulsion eyedrops are sterilized in an autoclave. Therefore, according to the present invention, it becomes possible to provide emulsion eyedrops which can be sterilized in an autoclave. Still furthermore, the eyedrops according to the present invention can keep the particle diameter thereof steadily even under thermally severe conditions such as conditions employed for sterilization in an autoclave, and does not undergo creaming even under conditions where a gravity load is applied by means of a centrifugation processing. Therefore, according to the present invention, it becomes also possible to provide stable emulsion eyedrops which does not change in the appearance thereof even when the emulsion eyedrops are stored for a long period. The method for stabilizing emulsion eyedrops according to the present invention can make it possible to stabilize emulsion eyedrops in such a manner that the emulsion eyedrops can keep the particle diameter thereof steadily even under thermally severe conditions such as conditions employed for sterilization in an autoclave, does not undergo creaming even under conditions where a gravity load is applied by means of a centrifugation processing, and does not change in the appearance thereof even when the emulsion eyedrops are stored for a long period.

DESCRIPTION OF EMBODIMENT

Hereinbelow, the embodiments of the present invention will be described.

The emulsion eyedrops according to the present invention contains 5 to 20 w/v % of castor oil and 2 to 7 w/v % of poly(vinyl alcohol), more preferably 5 to 10 w/v % of castor oil and 2 to 4 w/v % of poly(vinyl alcohol), wherein the ratio of the weight of castor oil to the weight of poly(vinyl alcohol) is 1.2 to 5. In the emulsion eyedrops according to the present invention, the ratio of the weight of castor oil to the weight of poly(vinyl alcohol) is preferably 2.5 to 5. It is preferred that the emulsion eyedrops according to the present invention contain substantially no nonionic surfactant. In the present invention, the term "emulsion eyedrops" refers to eyedrops in which castor oil is emulsified with poly(vinyl alcohol) so as to be uniformly dispersed in the form of fine oil droplets in an aqueous solution to form an oil-in-water type emulsion.

In this manner, emulsion eyedrops can be provided, which have a reduced risk of developing corneal disorders. Furthermore, emulsion eyedrops can also be provided, which have excellent thermal stability and physical stability and can contain a sparingly water-soluble drug in an increased amount.

The above-mentioned problems cannot be solved when any one of the types and contents of an oily component and an emulsifying agent and the content ratio between the oily component and the emulsifying agent are excluded from the scope of the present invention.

It is preferred for the emulsion eyedrops according to the present invention to contain a sparingly water-soluble drug.

It is preferred for the emulsion eyedrops according to the present invention that, when the emulsion eyedrops are sterilized in an autoclave at 121° C. for 20 minutes, the rate of change in the average particle diameter of oil droplets contained in the emulsion eyedrops before and after the sterilization in the autoclave is less than 3%, particularly preferably less than 2%, more preferably less than 1%.

It is preferred that the average particle diameter of oil droplets contained in the emulsion eyedrops according to the present invention before the sterilization in the autoclave is 100 to 200 nm.

In this case, the emulsion eyedrops can be filtrated using a filter for contaminants removal use during the production process of the emulsion eyedrops.

It is preferred for the emulsion eyedrops according to the present invention that, when the emulsion eyedrops are centrifuged at 20000×g for 20 minutes at 25° C., fine oil droplets are dispersed uniformly in the emulsion eyedrops.

Castor Oil

The castor oil to be used in the present invention is not particularly limited, as long as the castor oil is pharmacologically or physiologically acceptable. For example, castor oil produced from seeds by a known squeezing method or a known purification method or commercially available castor oil can be used. Castor oil that meets the standards of The Japanese Pharmacopoeia, Seventeenth Edition, is preferred.

Poly(Vinyl Alcohol)

The viscosity (4-w/w % solution) of poly(vinyl alcohol) to be used in the present invention is not particularly limited, and may be any one that is generally employed in the ophthalmic field. In general, the viscosity is 2 to 100 mm$^2$/s. In this regard, the viscosity (4-w/w % solution) of poly(vinyl alcohol) refers to a value obtained by cooling a solution prepared by dissolving poly(vinyl alcohol) in purified water at a concentration of 4 w/w % at 60 to 80° C. and then measuring the viscosity of the solution at 20 ±0.1° C. using a capillary viscometer (the provision in The Japanese Pharmacopoeia, Seventeenth Edition, a first viscosity measurement method). The poly(vinyl alcohol) to be used in the present invention may be a fully saponified product or a partially saponified product.

Nonionic Surfactant

The wording "containing (contain) substantially no nonionic surfactant" as used herein refers to the matter that no nonionic surfactant is contained or a nonionic surfactant is contained in such an amount that the emulsifying effect of the nonionic surfactant cannot be exerted sufficiently.

A nonionic surfactant refers to one which does not exhibit ionicity in a solution but has an interfacial activity and therefore can form micelles in a solution. Examples of the nonionic surfactant include: polyoxyethylene hydrogenated castor oil; and a polyoxyethylene sorbitan fatty acid ester, preferably polyoxyethylene sorbitan monooleate (e.g., polysorbate 80), polyoxyethylene sorbitan monolaurate, polyoxyethylene sorbitan monopalmitate and polyoxyethylene sorbitan monostearate.

Sparingly Water-Soluble Drug

The sparingly water-soluble drug to be used in the present invention is such drug that the volume of purified water to be required for dissolving 1 g of the drug at 25° C. and 1 atm is generally 1000 ml or more, preferably 10000 ml or more, more preferably 100000 ml or more. Namely, the term "a sparingly water-soluble drug" corresponds to the terms "very slightly soluble" or "practically insoluble" which is used for describing solubility in the Japanese Pharmacopoeia (The Japanese Pharmacopoeia, Seventeenth Edition, the provision, General Rule A-13, Hirokawa Shoten Ltd., 2016).

The sparingly water-soluble drug is not particularly limited, and may be selected appropriately from a steroid-type anti-inflammatory agent, a non-steroid-type anti-inflammatory agent, an anti-histamine agent, an anti-allergic agent, an antibacterial agent and the like, depending on the intended use. Among these sparingly water-soluble drugs, examples of the steroid-type anti-inflammatory agent include lotepredonol etabonate, fluorometholone, hydrocortisone, betamethasone, beclometasone propionate and fluticasone propionate.

In the emulsion eyedrops according to the present invention, the sparingly water-soluble drug is present in oil droplets (an oily phase). The content (concentration) of the sparingly water-soluble drug is not particularly limited, as long as the appearance of the emulsion cannot be affected. The sparingly water-soluble drug can be added to the emulsion eyedrops according to the present invention at a concentration corresponding to the saturated solubility of the sparingly water-soluble drug in castor oil. Specific concentration of the sparingly water-soluble drug may vary depending on the type of the sparingly water-soluble drug to be contained or the disease to be treated, and is generally 0.001% to 2%, preferably 0.01% to 1%, more preferably 0.1% to 0.5%.

Other Additives

The emulsion eyedrops according to the present invention can also contain additives that have been used commonly in eyedrops, as required. More specifically, examples of the additives include a buffering agent, a tonicity agent, a dissolution aid, a viscous base material, a chelating agent, a cooling agent, a pH modifier, a preservative agent and a stabilizing agent.

Examples of the buffering agent include a phosphate buffering agent, a borate buffering agent, a citrate buffering agent, a tartrate buffering agent, an acetate buffering agent, a Tris buffering agent and an amino acid.

Examples of the tonicity agent include: a sugar such as sorbitol, glucose and mannitol; a polyhydric alcohol such as glycerin and propylene glycol; a salt such as sodium chloride; and boric acid.

An example of the dissolution aid is a polyhydric alcohol such as glycerin and MACROGOL.

Examples of the viscous base material include: a water-soluble polymer such as poly(vinyl pyrrolidone), poly(ethylene glycol) and a carboxy vinyl polymer; and a cellulose such as hydroxyethyl cellulose, methyl cellulose, hydroxypropyl cellulose, hydroxypropyl methyl cellulose and carboxymethyl cellulose sodium.

Examples of the chelating agent include sodium edetate and citric acid.

Examples of the cooling agent include 1-menthol, borneol, camphor and eucalyptus oil.

Examples of the pH modifier include: an alkali such as sodium hydroxide and potassium hydroxide; and an acid such as acetic acid, citric acid, hydrochloric acid, phosphoric acid and tartaric acid.

Examples of the preservative agent include sorbic acid, potassium sorbate, sodium benzoate, methyl parahydroxybenzoate, ethyl parahydroxybenzoate, propyl parahydroxybenzoate, chlorobutanol, chlorhexidine gluconate, boric acid, dehydroacetic acid, sodium dehydroacetate, benzethonium chloride, benzyl alcohol, zinc chloride, parachlorometaxylenol, chlorocresol, phenethyl alcohol, polidronium chloride, thimerosal and sodium chlorite.

Examples of the stabilizing agent include poly(vinyl pyrrolidone), sodium sulfite, monoethanolamine, glycerin, propylene glycol, cyclodextrin, dextran, ascorbic acid, sodium edetate, taurine and tocopherol.

pH, Osmotic Pressure Ratio

The pH value and the osmotic pressure of the emulsion eyedrops according to the present invention are not particularly limited, as long as the pH value and the osmotic pressure respectively fall within acceptable ranges for eyedrops. More specifically, the pH value of the emulsion eyedrops according to the present invention is about 3 to 9, preferably about 4 to 8. The osmotic pressure of the emulsion eyedrops according to the present invention is such a value that the osmotic pressure ratio, i.e., the ratio of the osmotic pressure of the emulsion eyedrops to the osmotic pressure of physiological saline defined in the Japanese Pharmacopoeia, can become about 0.5 to 3, preferably about 0.9 to 1.1.

Appearance

The emulsion eyedrops according to the present invention are eyedrops in which castor oil is emulsified with poly(vinyl alcohol) and is dispersed uniformly in the form of fine oil droplets in an aqueous solution to form an oil-in-water type emulsion.

The average particle diameter of oil droplets in the emulsion eyedrops according to the present invention before the sterilization in an autoclave is preferably 50 to 500 nm, more preferably 100 to 200 nm, particularly preferably 130 to 180 nm. The measurement of the average particle diameter can be carried out using a particle diameter measurement device (a dynamic light scattering method).

Production Method

The emulsion eyedrops according to the present invention can be prepared by employing a known technique. For example, the emulsion eyedrops according to the present invention can be prepared by mixing and emulsifying castor oil having a sparingly water-soluble drug dispersed therein, poly(vinyl alcohol), arbitrary additives and water together. For performing the emulsification homogeneously, a known means such as a homomixer, a homogenizer, a microfluidizer and a high-pressure homogenizer can be used. The components for the emulsion eyedrops according to the present invention may be added in an arbitrary order.

Stabilization Method

The present invention also relates to an emulsion eyedrops stabilization method. The emulsion eyedrops stabilization method according to the present invention includes the step of preparing emulsion eyedrops containing castor oil and poly(vinyl alcohol), wherein the concentration of castor oil is 5 to 20 w/v %, the concentration of poly(vinyl alcohol) is 2 to 7 w/v %, and the ratio of the weight of castor oil to the weight of poly(vinyl alcohol) is 1.2 to 5. In the stabilization method, it is preferred that the content of castor oil is 5 to 10 w/v %, the content of poly(vinyl alcohol) is 2 to 4 w/v %, the ratio of the weight of castor oil to the weight of poly(vinyl alcohol) is 2.5 to 5 and substantially no nonionic surfactant is contained. In the stabilization method, the order of mixing of castor oil, poly(vinyl alcohol), water and other arbitrary additives or the method for mixing these components is not particularly limited, as long as the effect to stabilize can be achieved.

The term "stabilization" as used herein refers to the matter that emulsion eyedrops can keep the particle diameter thereof stably even under thermally severe conditions where the emulsion eyedrops are sterilized in an autoclave, and the emulsion eyedrops can also be prevented from the occurrence of creaming even under conditions where a gravity load is applied by a centrifugation processing.

In the stabilization method according to the present invention, it is preferred that, when the emulsion eyedrops are sterilized in an autoclave at 121° C. for 20 minutes, the rate of change in the average particle diameter of oil droplets contained in the emulsion eyedrops before and after the sterilization in the autoclave is less than 3%.

In the stabilization method according to the present invention, it is preferred that the average particle diameter of oil droplets contained in the emulsion eyedrops before the sterilization in an autoclave is 100 to 200 nm.

In the stabilization method according to the present invention, it is preferred that, when the emulsion eyedrops is centrifuged at 20000×g for 20 minutes, fine oil droplets are dispersed uniformly in the emulsion eyedrops.

In the stabilization method according to the present invention, it is preferred that the emulsion eyedrops further contain a sparingly water-soluble drug.

In the stabilization method according to the present invention, the method for the preparation of the emulsion eyedrops is not particularly limited. For example, the emulsion eyedrops can be prepared in accordance with the above-mentioned emulsion eyedrops production method. Alternatively, the emulsion eyedrops may also be prepared in accordance with the method mentioned below in the section "Test Example 1(1-1)".

In the stabilization method according to the present invention, the step or steps for confirming the achievement of stabilization may be included. For example, the stabilization method may also include the steps of: measuring the particle diameter of the emulsion eyedrops before the sterilization in an autoclave; measuring the particle diameter of the emulsion eyedrops after the sterilization in the autoclave; calculating the rate of change in particle diameter which is caused as the result of the sterilization in the autoclave; and observing the change in appearance of the emulsion eyedrops which is caused as the result of centrifugation. These steps can be carried out in accordance with the procedures mentioned below in the section "Test Example 1(1-2)(1-3)".

EXAMPLES

Hereinbelow, examples of the present invention will be described. In the following examples, the contents (%) of all of the components are expressed in w/v % unless otherwise specified.

Test Example 1

(1-1) Preparation of Emulsion, and Confirmation of Appearance of Emulsion

Each of water-soluble polymers, concentrated glycerin and sodium acetate hydrate were dissolved in purified water in accordance with the formulations shown in Tables 1 to 5 to prepare an aqueous phase. Castor oil was added to the aqueous phase while stirring the aqueous phase with T.K. ROBOMIX (manufactured by PRIMIX Corporation) (70° C., 8000 rpm, 15 minutes) to prepare a crude emulsion. The appearance of the crude emulsion was observed, and a crude emulsion which was completely emulsified was rated as "AA", a crude emulsion which was emulsified but had a small amount of oil droplets floated on the liquid surface thereof was rated as "A", a crude emulsion which was slightly emulsified but had an oil spread over the liquid surface thereof was rated as "B", and a crude emulsion which was not emulsified was rated as "F". A crude emulsion of which the appearance was rated as "AA" or "A" was atomized with Star Burst (manufactured by Sugino Machine Limited) (240 MPa, 20 passes), and the pH value of the resultant product was adjusted to 5.5 with hydrochloric acid or sodium hydroxide to produce an oil-in-water type emulsion.

(1-2) Change in Particle Diameter Due to Sterilization in Autoclave (AC Sterilization)

An oil-in-water type emulsion filled in a glass ampule was sterilized in an autoclave (121° C., 20 minutes), and then the average particle diameter (also simply referred to as "particle diameter", hereinafter) of oil droplets contained in the oil-in-water type emulsion each of before and after the sterilization in the autoclave was measured with Zetasizer Nano ZS (ZEN3600; manufactured by Malvern). As a sample for the measurement of the particle diameter, a solution prepared by diluting an oil-in-water type emulsion with purified water by 100-fold was used. An oil-in-water type emulsion of which the rate of change in particle diameter before and after the sterilization in an autoclave was less than 3% was rated as "A", an oil-in-water type emulsion of which the rate of change in particle diameter before and after the sterilization in an autoclave was 3% or more and less than 5% was rated as "B", and an oil-in-water type emulsion of which the rate of change in particle diameter before and after the sterilization in an autoclave was 5% or more was rated as "F". The results are shown in Tables 1 to 5.

Change (%) in particle diameter before and after AC sterilization=|(particle diameter after AC sterilization)−(particle diameter before AC sterilization)|/(particle diameter before AC sterilization)×100

(1-3) Change in Appearance Due to Centrifugation

An oil-in-water type emulsion was centrifuged at 25° C. under conditions of 13000 rpm (about 20000×g) for 20 minutes, and then the appearance of the centrifuged product was observed. A homogeneous solution was rated as "A", a solution in which the difference in density was observed in an upper part and a lower part was rated as "B", and a solution in which a creaming phase was observed was rated as "F". The results are shown in Tables 1 to 5.

TABLE 1

| g/100 mL | C. Ex. 1 | Ex. 1 | Ex. 2 | C. Ex. 2 |
|---|---|---|---|---|
| Castor oil | 5 | 5 | 5 | 5 |
| Poly(vinyl alcohol) (EG-05P) | 1 | 2 | 4 | 8 |
| Conc. Glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Evaluation of appearance upon crude emulsification | AA | AA | AA | AA |
| Particle diameter before AC sterilization | 202.8 nm | 169.6 nm | 136.0 nm | 84.2 nm |
| Particle diameter after AC sterilization | 206.7 nm | 170.0 nm | 137.2 nm | 90.7 nm |
| Rate of change in particle diameter before and after AC sterilization | 1.9% | 0.2% | 0.9% | 7.8% |
| Change in particle diameter due to AC sterilization | A | A | A | F |
| Change in appearance due to centrifugation | F | A | A | A |

TABLE 2

| g/100 mL | C. Ex. 3 | C. Ex. 4 | C. Ex. 5 | C. Ex. 6 |
|---|---|---|---|---|
| Castor oil | 5 | 5 | 5 | 5 |
| Poly(vinyl pyrrolidone) | 1 | 2 | 4 | 8 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Evaluation of appearance upon crude emulsification | B | B | B | F |
| Particle diameter before AC sterilization | | | | |
| Particle diameter after AC sterilization | | | | |
| Rate of change in particle diameter before and after AC sterilization | | | | |
| Change in particle diameter due to AC sterilization | | | | |
| Change in appearance due to centrifugation | | | | |

TABLE 3

| g/100 mL | C. Ex. 7 | C. Ex. 8 | C. Ex. 9 | C. Ex. 10 |
|---|---|---|---|---|
| Castor oil | 5 | 5 | 5 | 5 |
| Hypromellose (TC-5E) | 1 | 2 | 4 | 8 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Evaluation of appearance upon crude emulsification | B | B | A | AA |
| Particle diameter before AC sterilization | | | 419.8 nm | 272.5 nm |
| Particle diameter after AC sterilization | | | 489.9 nm | 322.1 nm |
| Rate of change in particle diameter before and after AC sterilization | | | 16.7% | 18.2% |
| Change in particle diameter due to AC sterilization | | | F | F |
| Change in appearance due to centrifugation | | | | |

TABLE 4

| g/100 mL | C. Ex. 11 | C. Ex. 12 | C. Ex. 13 | C. Ex. 14 |
|---|---|---|---|---|
| Castor oil | 5 | 5 | 5 | 5 |
| Hypromellose (60SH-50) | 0.5 | 1 | 2 | 4 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Evaluation of appearance upon crude emulsification | B | B | A | AA |
| Particle diameter before AC sterilization | | | 466.7 nm | 288.3 nm |
| Particle diameter after AC sterilization | | | 609.4 nm | 426.4 nm |
| Rate of change in particle diameter before and after AC sterilization | | | 30.6% | 47.9% |
| Change in particle diameter due to AC sterilization | | | F | F |
| Change in appearance due to centrifugation | | | | |

TABLE 5

| g/100 mL | C. Ex. 15 | C. Ex. 16 | C. Ex. 17 | C. Ex. 18 |
|---|---|---|---|---|
| Castor oil | 5 | 5 | 5 | 5 |
| Carmellose sodium | 0.1 | 0.5 | 1 | 2 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Evaluation of appearance upon crude emulsification | F | F | F | F |
| Particle diameter before AC sterilization | | | | |
| Particle diameter after AC sterilization | | | | |
| Rate of change in particle diameter before and after AC sterilization | | | | |
| Change in particle diameter due to AC sterilization | | | | |
| Change in appearance due to centrifugation | | | | |

As shown in Tables 1 to 5, the appearances of crude emulsions each containing 1 to 8% of poly(vinyl alcohol) and 4 to 8% of hypromellose (TC-5E) or 2 to 4% of hypromellose (60 SH-50) was good. Some of the crude emulsions each having a good appearance were atomized, and were evaluated with respect to the change in particle diameter due to the sterilization in an autoclave (AC sterilization) and the change in appearance due to centrifugation. As a result, emulsions each containing 2 to 4% of poly(vinyl alcohol) showed good results. It was demonstrated that, among formulations each containing 5% of castor oil, only formulations each containing 2 to 4% of poly(vinyl alcohol) as a water-soluble polymer were stable oil-in-water type emulsions.

Test Example 2

Oil-in-water type emulsions were prepared in accordance with the formulations shown in Tables 6 to 8. The method for the preparation was the same as that employed in Test Example 1(1-1). All of the appearances of products upon crude emulsification were rated as "AA". Atomized oil-in-water type emulsions were evaluated with respect to the change in particle diameter due to the sterilization in an autoclave (AC sterilization) and the change in appearance due to centrifugation by the same methods as those employed in Test Examples 1(1-2) and (1-3). The results are shown in Tables 6 to 8.

TABLE 6

| g/100 mL | C. Ex. 19 | Ex. 3 | Ex. 4 | Ex. 5 |
|---|---|---|---|---|
| Castor oil | 5 | 10 | 10 | 10 |
| Poly(vinyl alcohol) (EG-05P) | 5 | 2 | 4 | 5 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Particle diameter before AC sterilization | 117.8 nm | 188.7 nm | 148.3 nm | 133.2 nm |
| Particle diameter after AC sterilization | 122.5 nm | 189.1 nm | 150.2 nm | 136.3 nm |
| Rate of change in particle diameter before and after AC sterilization | 4.0% | 0.2% | 1.3% | 2.3% |
| Change in particle diameter due to AC sterilization | B | A | A | A |
| Change in appearance due to centrifugation | A | A | A | A |

TABLE 7

| g/100 mL | Ex. 6 | C. Ex. 20 | C. Ex. 21 |
|---|---|---|---|
| Castor oil | 10 | 10 | 20 |
| Poly(vinyl alcohol) (EG-05P) | 7 | 8 | 2 |
| Conc. glycerin | 2.2 | 2.2 | 2.2 |
| Sodium acetate hydrate | 0.05 | 0.05 | 0.05 |
| Purified water | q.l. | q.l. | q.l. |
| pH | 5.5 | 5.5 | 5.5 |
| Particle diameter before AC sterilization | 111.6 nm | 100.7 nm | 214.6 nm |
| Particle diameter after AC sterilization | 113.2 nm | 104.2 nm | 218.6 nm |
| Rate of change in particle diameter before and after AC sterilization | 1.4% | 3.5% | 1.9% |
| Change in particle diameter due to AC sterilization | A | B | A |
| Change in appearance due to centrifugation | A | A | B |

TABLE 8

| g/100 mL | Ex. 7 | C. Ex. 22 | C. Ex. 23 | C. Ex. 24 |
|---|---|---|---|---|
| Castor oil | 20 | 30 | 30 | 30 |
| Poly(vinyl alcohol) (EG-05P) | 4 | 1 | 2 | 4 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Particle diameter before AC sterilization | 177.4 nm | 414.2 nm | 281.2 nm | 213.0 nm |
| Particle diameter after AC sterilization | 181.8 nm | 438.7 nm | 278.8 nm | 213.3 nm |
| Rate of change in particle diameter before and after AC sterilization | 2.5% | 5.9% | 0.9% | 0.1% |
| Change in particle diameter due to AC sterilization | A | F | A | A |
| Change in appearance due to centrifugation | A | F | B | B |

The relationship among the concentrations of castor oil and poly(vinyl alcohol), the ratio of the weight of castor oil to the weight of poly(vinyl alcohol) (C/P), the rate of change in particle diameter due to the sterilization in an autoclave and the change in appearance due to centrifugation, which were obtained based on the results of Test Example 1 and Test Example 2, are shown in Table 9.

TABLE 9

| | | Concentration of poly(vinyl alcohol) (P) (w/v %) | | | | | |
|---|---|---|---|---|---|---|---|
| Test No.[*4] | | 1 | 2 | 4 | 5 | 7 | 8 |
| Concentration of castor oil (C) (w/v %) | 5 | 1.9% F<br>c/p = 5<br>C. Ex. 1 | 0.2% A<br>c/p = 2.5<br>Ex. 1 | 0.9% A<br>c/p = 1.25<br>Ex. 2 | 4.0% A<br>c/p = 1<br>C. Ex. 19 | | 7.8% A<br>c/p = 0.63<br>C. Ex. 2 |
| | 10 | | 0.2% A<br>c/p = 5<br>Ex. 3 | 1.3% A<br>c/p = 2.5<br>Ex. 4 | 2.3% A<br>c/p = 2<br>Ex. 5 | 1.4% A<br>c/p = 1.43<br>Ex. 6 | 3.5% A<br>c/p = 1.25<br>C. Ex. 20 |
| | 20 | | 1.9% B<br>c/p = 10<br>C. Ex. 21 | 2.5% A<br>c/p = 5<br>Ex. 7 | | | |
| | 30 | 5.9% F<br>c/p = 30<br>C. Ex. 22 | 0.9% B<br>c/p = 15<br>C. Ex. 23 | 0.1% B<br>c/p = 7.5<br>C. Ex. 24 | | | |

Header notes for Table 9: Rate of change in particle diameter[*1] / Change in appearance[*2] / c/p[*3]

[*1] Rate of change in particle diameter before and after AC sterilization
[*2] Change in appearance due to centrifugation
[*3] Rate of weight of castor oil to weight of poly(vinyl alcohol)
[*4] Example No. or Comparative Example No.

Emulsions each containing 5 to 30% of castor oil and 1 to 8% of poly(vinyl alcohol) were evaluated with respect to the change in particle diameter due to the sterilization in an autoclave (AC sterilization) and the change in appearance due to centrifugation. The emulsions each containing 5 to 20% of castor oil and 2 to 7% of poly(vinyl alcohol) showed good results. However, even when castor oil and poly(vinyl alcohol) were used in concentrations respectively falling within the above-mentioned ranges, unstable emulsions were produced (Comparative Example 19 and Comparative Example 21).

It was demonstrated that only the formulations each of which contained 5 to 20% of castor oil and 2 to 7% of poly(vinyl alcohol) and in each of which the ratio of the weight of castor oil to the weight of poly(vinyl alcohol) was 1.25 to 5 were stable oil-in-water type emulsions.

Test Example 3

Oil-in-water type emulsions were prepared in accordance with the formulations shown in Table 10 to Table 12. The method for the preparation was the same as that employed in Test Example 1(1-1). The appearances of all of the emulsions upon the crude emulsification were rated as "AA". Each of the atomized oil-in-water type emulsions was evaluated with respect to the change in particle diameter due to the sterilization in an autoclave (AC sterilization) and the change in appearance due to centrifugation in the same manner as in Test Examples 1(1-2) and (1-3). The results are shown in Tables 10 to 12.

TABLE 10

| g/100 mL | C. Ex. 25 | C. Ex. 26 | C. Ex. 27 | C. Ex. 28 | C. Ex. 29 |
| --- | --- | --- | --- | --- | --- |
| Corn oil | 20 | — | — | — | — |
| Soybean oil | — | 20 | — | — | — |
| Cotton seed oil | — | — | 20 | — | — |
| Sesame oil | — | — | — | 20 | — |
| Olive oil | — | — | — | — | 20 |
| Poly(vinyl alcohol) (EG-05P) | 4 | 4 | 4 | 4 | 4 |
| Conc. glycerin | 2.2 | 2.2 | 2.2 | 2.2 | 2.2 |
| Sodium acetate hydrate | 0.05 | 0.05 | 0.05 | 0.05 | 0.05 |
| Purified water | q.l. | q.l. | q.l. | q.l. | q.l. |
| pH | 5.5 | 5.5 | 5.5 | 5.5 | 5.5 |
| Particle diameter before AC sterilization | 168.6 nm | 179.0 nm | 174.0 nm | 168.1 nm | 174.3 nm |
| Particle diameter after AC sterilization | 171.3 nm | 175.5 nm | 177.9 nm | 172.8 nm | 177.8 nm |
| Rate of change in particle diameter before and after AC sterilization | 1.6% | 2.0% | 2.2% | 2.8% | 2.0% |
| Change in particle diameter due to AC sterilization | A | A | A | A | A |
| Change in appearance due to centrifugation | F | F | F | F | F |

TABLE 11

| g/100 mL | C. Ex. 30 | C. Ex. 31 | C. Ex. 32 | C. Ex. 33 |
| --- | --- | --- | --- | --- |
| Palm oil | 20 | — | — | — |
| Squalane | — | 20 | — | — |
| Oleyl alcohol | — | — | 20 | — |
| Isopropyl myristate | — | — | — | 20 |
| Poly(vinyl alcohol) (EG-05P) | 4 | 4 | 4 | 4 |
| Conc. glycerin | 2.2 | 2.2 | 2.2 | 2.2 |
| Sodium acetate hydrate | 0.05 | 0.05 | 0.05 | 0.05 |
| Purified water | q.l. | q.l. | q.l. | q.l. |
| pH | 5.5 | 5.5 | 5.5 | 5.5 |
| Particle diameter before AC sterilization | 168.3 nm | 182.0 nm | 288.4 nm | 346.4 nm |
| Particle diameter after AC sterilization | 174.0 nm | 206.2 nm | 618.3 nm | 807.7 nm |
| Rate of change in particle diameter before and after AC sterilization | 3.4% | 13.3% | 114.4% | 133.2% |
| Change in particle diameter due to AC sterilization | F | F | F | F |
| Change in appearance due to centrifugation | F | F | F | F |

TABLE 12

| g/100 mL | C. Ex. 34 | C. Ex. 35 |
| --- | --- | --- |
| Miglyol 812 | 5 | 20 |
| Poly(vinyl alcohol) (EG-05P) | 2 | 4 |
| Conc. glycerin | 2.2 | 2.2 |
| Sodium acetate hydrate | 0.05 | 0.05 |
| Purified water | q.l. | q.l. |
| pH | 5.5 | 5.5 |
| Particle diameter before AC sterilization | 140.5 nm | 163.0 nm |
| Particle diameter after AC sterilization | 175.9 nm | 195.7 nm |
| Rate of change in particle diameter before and after AC sterilization | 25.2% | 20.1% |
| Change in particle diameter due to AC sterilization | F | F |
| Change in appearance due to centrifugation | F | F |

As shown in Tables 10 to 12, emulsions each containing 20% of each of various oily components and 4% of poly(vinyl alcohol) were evaluated with respect to the change in particle diameter due to the sterilization in an autoclave (AC sterilization) and the change in appearance due to centrifugation. Emulsions each containing an oily component other than castor oil did not show good results. It was demonstrated that only formulations each containing castor oil as the oily component were stable oil-in-water type emulsions.

Test Example 4

Oil-in-water type emulsions were prepared in accordance with the formulations shown in Table 13. The method for the preparation was the same as that employed in Test Example 1(1-1). The appearances of all of the emulsions upon the crude emulsification were rated as "AA". The atomized oil-in-water type emulsions were evaluated with respect to the change in particle diameter due to the sterilization in an autoclave (AC sterilization) and the change in appearance due to centrifugation in the same manner as in Test Examples 1(1-2) and (1-3). The results are shown in Table 13.

Test Example 5

Freezing-and-Thawing Test

Each of the oil-in-water type emulsion of Example 3, which showed the smallest change in particle diameter in the results of Test Example 1, and the oil-in-water type emulsion of Comparative Example 21, which was a comparative emulsion for the emulsion of Example 3, was subjected to a freezing-and-thawing test. Each of the oil-in-water type emulsions which was filled in a glass ampule was placed in a store chamber at -30° C. to freeze the oil-in-water type emulsion. The frozen oil-in-water type emulsion was thawed at room temperature, and the appearance of the oil-in-water type emulsion after the thawing was observed. A homogeneous emulsion in which creaming did not occur was rated as "AA", an emulsion in which the separation of an oily phase did not occur but creaming occurred was rated as "A", and an emulsion in which phase separation into a transparent

TABLE 13

| g/100 mL | C. Ex. 36 | C. Ex. 37 | C. Ex. 38 | C. Ex. 39 | C. Ex. 40 |
| --- | --- | --- | --- | --- | --- |
| Castor oil | 5 | 5 | 5 | 5 | 5 |
| Hypromellose acetate succinate (AS-MF) | 4 | — | — | — | — |
| Poly(ethylene glycol) graft copolymer (Soluplus) | — | 4 | — | — | — |
| Hypromellose phthalate (HP-50) | — | — | 4 | — | — |
| Polyoxyethylene hydrogenated castor oil (HCO-60) | — | — | — | 4 | — |
| Polyoxyl 40 stearate | — | — | — | — | 4 |
| Conc. glycerin | 2.2 | 2.2 | 2.2 | 2.2 | 2.2 |
| Boric acid | 0.4 | 0.4 | 0.4 | — | — |
| Borax | 0.2 | 0.2 | 0.2 | — | — |
| Sodium acetate hydrate | — | — | — | 0.05 | 0.05 |
| Purified water | q.l. | q.l. | q.l. | q.l. | q.l. |
| pH | 7.5 | 7.5 | 7.5 | 5.5 | 5.5 |
| Particle diameter before AC sterilization | 210.5 nm | 266.4 nm | 256.3 nm | 86.36 nm | 118.3 nm |
| Particle diameter after AC sterilization | 186.1 nm | 550.7 nm | 259.3 nm | 1154 nm | — (*5) |
| Rate of change in particle diameter before and after AC sterilization | 11.6% | 106.7% | 1.2% | 1236.3% | — |
| Change in particle diameter due to AC sterilization | F | F | A | F | F |
| Change in appearance due to centrifugation | F | F | F | F | F |

(*5) Phase separation occurred and therefore particle diameters could not be measured.

As shown in Table 13, emulsions respectively containing hypromellose acetate succinate (AS-MF), poly(ethylene glycol) graft copolymer (Soluplus), hypromellose phthalate (HP-50), polyoxyethylene hydrogenated castor oil (HCO-60) and Polyoxyl 40 stearate at a concentration of 4% were evaluated with respect to the change in particle diameter due to the sterilization in an autoclave (AC sterilization) and the change in appearance due to centrifugation. In all of Comparative Example 36 to Comparative Example 40, good results were not obtained. It was demonstrated that only the formulation using poly(vinyl alcohol) as the emulsifying agent was a stable oil-in-water type emulsion.

oily phase and a clouded aqueous phase was rated as "F". The results are shown in Table 14.

TABLE 14

| g/100 mL | Ex. 3 | C. Ex. 21 |
| --- | --- | --- |
| Castor oil | 10 | 20 |
| Poly(vinyl alcohol) (EG-05P) | 2 | 2 |
| Conc. glycerin | 2.2 | 2.2 |
| Sodium acetate hydrate | 0.05 | 0.05 |
| Purified water | q.l. | q.l. |
| pH | 5.5 | 5.5 |
| Change in appearance | AA | F |

As shown in Table 14, as the result of the evaluation on the change in appearance in the freezing-and-thawing test, good results were obtained in the formulations in each of which the ratio of the weight of castor oil to the weight of poly(vinyl alcohol) was 5 or less.

Preparation Examples

Emulsion eyedrops of Examples 8 to 10 were prepared in accordance with the formulations shown in Table 15 by performing the same procedure as that in Test Example 1(1-1), except that the step of dissolving a drug in castor oil was added.

TABLE 15

| g/100 mL | Ex. 8 | Ex. 9 | Ex. 10 |
|---|---|---|---|
| Ciprofloxacin | 0.3 | — | — |
| Indometacin | — | 0.3 | — |
| Fluorometholone | — | — | 0.02 |
| Castor oil | 10 | 20 | 20 |
| Poly(vinyl alcohol) (EG-05P) | 2 | 4 | 4 |
| Sodium acetate hydrate | 0.1 | 0.1 | — |
| Sodium hydrogenphosphate | — | — | 0.1 |
| Glycerin | 1 | — | 2 |
| Sodium chloride | 0.45 | 0.9 | — |
| Sorbic acid | 0.1 | 0.1 | — |
| Sodium edetate | 0.02 | — | — |
| pH | 5 | 5 | 7 |

The embodiments and examples disclosed above are to be considered as illustrative only and not restrictive in all respects. The scope of the invention is defined by the claims rather than by the foregoing embodiments and examples, and all modifications and changes that fall within meets and bounds of the claims, or equivalence of such meets and bounds are therefore intended to be embraced by the claims.

The invention claimed is:

1. Emulsion eyedrops comprising castor oil and poly(vinyl alcohol), wherein the concentration of the castor oil is 5 to 20 w/v %, the concentration of the poly(vinyl alcohol) is 2 to 7 w/v %, the ratio of the weight of the castor oil to the weight of the poly(vinyl alcohol) is 1.2 to 5,
   wherein no nonionic surfactant is present,
   wherein the average particle diameter of oil droplets contained in the emulsion eyedrops before the sterilization in the autoclave is 100 to 200 nm,
   wherein the emulsion eyedrops do not contain water-soluble polymers other than poly(vinyl alcohol),
   and wherein, when the emulsion eyedrops are sterilized in an autoclave at 121° C. for 20 minutes, the rate of change in the average particle diameter of oil droplets contained in the emulsion eyedrops before and after the sterilization in the autoclave is less than 3%.

2. The emulsion eyedrops according to claim 1, wherein a sparingly water-soluble drug is further contained.

3. The emulsion eyedrops according to claim 1, wherein, when the emulsion eyedrops are centrifuged at 20000×g for 20 minutes, the emulsion eyedrops are homogeneous.

4. An emulsion eyedrops stabilization method, comprising the step of preparing emulsion eyedrops containing castor oil and poly(vinyl alcohol), wherein:
   the concentration of the castor oil is 5 to 20 w/v %;
   the concentration of the poly(vinyl alcohol) is 2 to 7 w/v %; and
   the ratio of the weight of the castor oil to the weight of the poly(vinyl alcohol) is 1.2 to 5, wherein no nonionic surfactant is present, wherein the average particle diameter of oil droplets contained in the emulsion eyedrops before the sterilization in the autoclave is 100 to 200 nm, wherein the emulsion eyedrops do not contain water-soluble polymers other than poly(vinyl alcohol), and wherein, when the emulsion eyedrops are sterilized in an autoclave at 121° C. for 20 minutes, the rate of change in the average particle diameter of oil droplets contained in the emulsion eyedrops before and after the sterilization in the autoclave is less than 3%.

5. The stabilization method according to claim 4, wherein the emulsion eyedrops further contain a sparingly water-soluble drug.

6. The stabilization method according to claim 4, wherein, when the emulsion eyedrops are centrifuged at 20000×g for 20 minutes, the emulsion eyedrops are homogeneous.

* * * * *